(12) United States Patent
Bloom et al.

(10) Patent No.: US 7,316,706 B2
(45) Date of Patent: Jan. 8, 2008

(54) TENSIONING DEVICE, SYSTEM, AND METHOD FOR TREATING MITRAL VALVE REGURGITATION

(75) Inventors: Eliot Bloom, Hopkinton, NH (US); Nareak Douk, Lowell, MA (US); John Horrigan, Beverly, MA (US); Rany Huynh, Brighton, MA (US); Nasser Rafiee, Andover, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 639 days.

(21) Appl. No.: 10/867,394

(22) Filed: Jun. 14, 2004

(65) Prior Publication Data

US 2004/0260317 A1 Dec. 23, 2004

Related U.S. Application Data

(60) Provisional application No. 60/480,195, filed on Jun. 20, 2003, provisional application No. 60/480,472, filed on Jun. 20, 2003, provisional application No. 60/503,035, filed on Sep. 15, 2003.

(51) Int. Cl.
*A61B 17/04* (2006.01)
*A61B 17/08* (2006.01)

(52) U.S. Cl. .................... 606/232; 606/151

(58) Field of Classification Search ............ 606/232, 606/72, 74, 103, 228–230, 172; 24/115 R, 24/129 W, 136 R, 115 A, 132 R; 607/126–128, 607/132; 604/164.05
See application file for complete search history.

(56) References Cited

U.S. PATENT DOCUMENTS 4,437,475 A * 3/1984 White ...................... 607/126

| | | | |
|---|---|---|---|
| 4,581,019 A * | 4/1986 | Curelaru et al. | 604/164.05 |
| 5,626,611 A * | 5/1997 | Liu et al. | 606/230 |
| 5,853,422 A | 12/1998 | Heubsch et al. | |
| 5,879,366 A | 3/1999 | Shaw et al. | |
| 5,928,250 A | 7/1999 | Koike et al. | |
| 5,944,738 A | 8/1999 | Amplatz et al. | |
| 5,961,440 A | 10/1999 | Schweich, Jr. et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,155,968 A | 12/2000 | Wilk | |

(Continued)

FOREIGN PATENT DOCUMENTS

WO    WO 00/60995    10/2000

(Continued)

*Primary Examiner*—Julian W. Woo (57) ABSTRACT

A system for treating mitral valve regurgitation comprises a tensioning device slidably received within a delivery catheter. The tensioning device includes a tether linking proximal an anchoring member and a distal anchoring member. At least one of the anchoring members includes an elastic portion that flexes in response to a heartbeat when the tensioning device is positioned across a chamber of a heart. The tether includes at least one locking member initially positioned between the anchoring members. A method for treating mitral valve regurgitation comprises piercing a first wall of a chamber of a heart, engaging a distal anchoring member with a second wall of the heart chamber, engaging a proximal anchoring member with the first wall, and pulling a locking member affixed to a tether linking the anchoring members from an initial position between the two anchoring members to a locked position proximal the proximal anchoring member.

13 Claims, 7 Drawing Sheets

U.S. PATENT DOCUMENTS

| | | | |
|---|---|---|---|
| 6,162,168 A | 12/2000 | Schweich, Jr. et al. | |
| 6,165,120 A | 12/2000 | Schweich, Jr. et al. | |
| 6,171,329 B1 | 1/2001 | Shaw et al. | |
| 6,210,432 B1 | 4/2001 | Solem et al. | |
| 6,258,021 B1 | 7/2001 | Wilk | |
| 6,260,552 B1 | 7/2001 | Mortier et al. | |
| 6,261,222 B1 | 7/2001 | Schweich, Jr. et al. | |
| 6,332,863 B1 | 12/2001 | Schweich, Jr. et al. | |
| 6,406,420 B1 | 6/2002 | McCarthy et al. | |
| 6,491,714 B1 * | 12/2002 | Bennett | 606/232 |
| 6,537,198 B1 | 3/2003 | Vidlund et al. | |
| 6,565,603 B2 | 5/2003 | Cox | |
| 6,569,198 B1 | 5/2003 | Wilson et al. | |
| 6,656,603 B2 | 5/2003 | Cox | |
| 6,572,529 B2 | 6/2003 | Wilk | |
| 6,589,160 B2 | 7/2003 | Schweich, Jr. et al. | |
| 6,616,684 B1 | 9/2003 | Vidlund et al. | |
| 6,661,684 B2 | 9/2003 | Vidllund et al. | |
| 6,629,921 B1 | 10/2003 | Schweich, Jr. et al. | |
| 6,723,038 B1 | 4/2004 | Schroeder et al. | |
| 6,764,510 B2 | 7/2004 | Vidlund et al. | |
| 6,776,754 B1 | 8/2004 | Wilk | |
| 6,802,319 B2 | 10/2004 | Stevens et al. | |
| 6,908,478 B2 | 6/2005 | Alferness et al. | |
| 7,044,905 B2 | 5/2006 | Vidlund et al. | |
| 2001/0016675 A1 | 8/2001 | Mortier et al. | |
| 2001/0025171 A1 | 9/2001 | Mortier et al. | |
| 2001/0041916 A1 * | 11/2001 | Bonutti | 606/232 |
| 2002/0058855 A1 | 5/2002 | Schweich et al. | |
| 2002/0077524 A1 | 6/2002 | Schweich et al. | |
| 2002/0169359 A1 | 11/2002 | McCarthy et al. | |
| 2002/0188170 A1 | 12/2002 | Santamore et al. | |
| 2003/0032979 A1 | 2/2003 | Mortier et al. | |
| 2003/0105520 A1 | 6/2003 | Alferness et al. | |
| 2003/0158570 A1 | 8/2003 | Ferrazzi | |
| 2003/0166992 A1 | 9/2003 | Schweich et al. | |
| 2003/0171641 A1 | 9/2003 | Schweich et al. | |
| 2003/0181928 A1 | 9/2003 | Vidlund et al. | |
| 2004/0127983 A1 | 7/2004 | Mortier et al. | |
| 2004/0133063 A1 | 7/2004 | McCarthy et al. | |
| 2004/0225304 A1 | 11/2004 | Vidlund et al. | |
| 2004/0260317 A1 | 12/2004 | Bloom et al. | |
| 2005/0075723 A1 | 4/2005 | Schroeder et al. | |
| 2005/0148815 A1 | 7/2005 | Mortier et al. | |
| 2006/0089711 A1 | 4/2006 | Dolan | |
| 2006/0149123 A1 | 7/2006 | Vidlund et al. | |
| 2006/0161040 A1 | 7/2006 | McCarthy et al. | |

FOREIGN PATENT DOCUMENTS

| | | |
|---|---|---|
| WO | WO02/076284 | 10/2002 |

* cited by examiner

TENSIONING DEVICE, SYSTEM, AND METHOD FOR TREATING MITRAL VALVE REGURGITATION

PRIORITY CLAIM

This application claims the benefit of U.S. Provisional Application No. 60/480,195 filed Jun. 20, 2003; U.S. Provisional Application No. 60/480,472 filed Jun. 20, 2003; and U.S. Provisional Application No. 60/503,035 filed Sep. 15, 2003; the entirety of each of which is hereby incorporated by reference.

TECHNICAL FIELD

This invention relates generally to medical devices and particularly to a system and method for treating mitral valve regurgitation.

BACKGROUND OF THE INVENTION

The heart is a four-chambered pump that moves blood efficiently through the vascular system. Blood enters the heart through the vena cava and flows into the right atrium. From the right atrium, blood flows through the tricuspid valve and into the right ventricle, which then contracts and forces blood through the pulmonic valve and into the lungs. Oxygenated blood returns from the lungs and enters the heart through the left atrium and passes through the bicuspid mitral valve into the left ventricle. The left ventricle contracts and pumps blood through the aortic valve into the aorta and to the vascular system.

The mitral valve consists of two leaflets (anterior and posterior) attached to a fibrous ring or annulus. In a healthy heart, the mitral valve leaflets overlap during contraction of the left ventricle and prevent blood from flowing back into the left atrium. However, due to various cardiac diseases, the mitral valve annulus may become distended, causing the leaflets to remain partially open during ventricular contraction and thus allowing regurgitation of blood into the left atrium. This results in reduced ejection volume from the left ventricle, causing the left ventricle to compensate with a larger stroke volume. The increased workload eventually results in dilation and hypertrophy of the left ventricle, further enlarging and distorting the shape of the mitral valve. If left untreated, the condition may result in cardiac insufficiency, ventricular failure, and death.

It is common medical practice to treat mitral valve regurgitation by valve replacement or repair. Valve replacement involves an open-heart surgical procedure in which the patient's mitral valve is removed and replaced with an artificial valve. This is a complex, invasive surgical procedure with the potential for many complications and a long recovery period.

Mitral valve repair includes a variety of procedures to repair or reshape the leaflets to improve closure of the valve during ventricular contraction. If the mitral valve annulus has become distended, a common repair procedure involves implanting an annuloplasty ring on the mitral valve annulus. The annuloplasty ring generally has a smaller diameter than the annulus, and when sutured to the annulus, the annuloplasty ring draws the annulus into a smaller configuration, bringing the mitral valve leaflets closer together and providing improved closure during ventricular contraction.

Annuloplasty rings may be rigid, flexible, or have both rigid and flexible segments. Rigid annuloplasty rings have the disadvantage of causing the mitral valve annulus to be rigid and unable to flex in response to the contractions of the ventricle, thus inhibiting the normal movement of the mitral valve that is required for it to function optimally. Flexible annuloplasty rings are frequently made of Dacron® fabric and must be sewn to the annular ring with a line of sutures. This eventually leads to scar tissue formation and loss of flexibility and function of the mitral valve. Similarly, combination rings must generally be sutured in place and also cause scar tissue formation and loss of mitral valve flexibility and function.

Annuloplasty rings have been developed that do not require suturing. U.S. Pat. No. 6,565,603 discloses a combination rigid and flexible annuloplasty ring that is inserted into the fat pad of the atrioventricular groove, which surrounds the mitral valve annulus. Although this device avoids the need for sutures, it must be placed within the atrioventricular groove with great care to prevent tissue damage to the heart.

U.S. Pat. No. 6,569,198 discloses a flexible annuloplasty ring designed to be inserted into the coronary sinus, which is located adjacent to and partially surrounds the mitral annulus. The prosthesis is shortened lengthwise within the coronary sinus to reduce the size of the mitral annulus. However, the coronary sinus in a particular individual may not wrap around the heart far enough to allow effective encircling of the mitral valve, making this treatment ineffective.

U.S. Pat. No. 6,210,432 discloses a flexible elongated device that is inserted into the coronary sinus and adapts to the shape of the coronary sinus. The device then undergoes a change that causes it to assume a reduced radius of curvature and, as a result, causes the radius of curvature of the coronary sinus and the circumference of the mitral annulus to be reduced. While likely to be effective for modest changes in the size or shape of the mitral annulus, this device may cause significant tissue compression in patients requiring a larger change in the configuration of the mitral annulus.

U.S. patent application Publication No. 2003/0105520 discloses a flexible elongated device that is inserted into the coronary sinus and anchored at each end by a self-expanding, toggle bolt-like anchor that expands and engages the inner wall of the coronary sinus. Application WO02/076284 discloses a similar flexible elongated device that is inserted into the coronary sinus. This device is anchored at the distal end by puncturing the wall of the coronary sinus, crossing the intervening cardiac tissue, and deploying the anchor against the exterior of the heart in the pericardial space. The proximal end of the elongated member is anchored against the coronary ostium, which connects the right atrium and the coronary sinus. Once anchored at each end, the length of either of the elongated devices may be adjusted to reduce the curvature of the coronary sinus and thereby change the configuration of the mitral annulus. Due to the nature of the anchors, both of these devices may cause significant damage to the coronary sinus and surrounding cardiac tissue. Also, leaving a device in the coronary sinus may result in formation and breaking off of a thrombus that may pass into the right atrium, right ventricle, and ultimately the lungs, causing a pulmonary embolism. Another disadvantage is that the coronary sinus is typically used for placement of a pacing lead, which may be precluded with the placement of the prosthesis in the coronary sinus.

U.S. Pat. No. 6,616,684 discloses a splint assembly that is positioned transverse the left ventricle to treat mitral valve leakage. In one embodiment, the assembly is delivered through the right ventricle. One end of the assembly is anchored outside the heart, resting against the outside wall of the left ventricle, while the other end is anchored within the right ventricle, against the septal wall. The heart-engaging portions of the assembly, i.e., the anchors, are essentially flat and lie snugly against their respective walls. The length of the splint assembly is either preset or is adjusted to draw the two walls of the chamber toward each other.

The splint assembly may be delivered endovascularly, which offers distinct advantages over open surgery methods. However, the endovascular delivery technique is complicated, involving multiple delivery steps and devices, and requiring that special care be taken to avoid damage to the pericardium and lungs. First, a needle or guidewire is delivered into the right ventricle, advanced through the septal wall, and anchored to the outer or free wall of the left ventricle using barbs or threads that are rotated into the tissue of the free wall. Visualization is required to ensure the needle does not cause damage beyond the free wall. A delivery catheter is then advanced over the needle, piercing both the septal wall and the free wall of the ventricle. The catheter is anchored to the free wall with balloons inflated on either side of the wall. A tension member is then pushed through the delivery catheter such that a distal anchor is positioned outside the heart. During the catheter anchoring and distal anchor positioning steps, care must be taken to guard against damaging the pericardium or lungs, and insufflation of the space between the myocardium and the pericardial sac may be desirable. A securing band is advanced over the tension member to expand the distal anchor and/or maintain it in an expanded configuration. The catheter is withdrawn, and a second (proximal) anchor is advanced over the tension member using a deployment tool and positioned within the right ventricle against the septal wall. A tightening device then holds the second anchor in a position so as to alter the shape of the left ventricle. Excess length of the tension member is thermally severed prior to removal, again posing some risk to tissue in and around the heart.

Therefore, it would be desirable to provide a system and method for treating mitral valve regurgitation that overcome the aforementioned and other disadvantages.

SUMMARY OF THE INVENTION

One aspect of the present invention is a tensioning device for treating mitral valve regurgitation, comprising a tether and proximal and distal anchoring members. The distal anchoring member is positioned adjacent to a distal end of the tether, and the proximal anchoring member is positioned adjacent to a proximal end of the tether. At least one of the anchoring members includes an elastic portion that flexes in response to a heartbeat when the tensioning device is positioned across a chamber of a heart.

Another aspect of the present invention is a system for treating mitral valve regurgitation that includes the above-described tensioning device and further comprises a delivery catheter. The tensioning device is slidably received within a lumen of the delivery catheter.

The present invention includes another system for treating mitral valve regurgitation that comprises a delivery catheter and a tensioning device slidably received within a lumen of the delivery catheter. The tensioning device includes a tether and proximal and distal anchoring members, the distal anchoring member positioned adjacent to a distal end of the tether, and the proximal anchoring member positioned adjacent to a proximal end of the tether. At least one locking member is affixed to the tether. When the locking member is pulled from an initial position between the anchoring members to a locked position proximal the proximal anchoring member, the length of the tether is adjusted to change the proximity of the anchoring members one to the other.

Another aspect of the present invention is a method of treating mitral valve regurgitation by affecting a mitral valve annulus. A first wall of a chamber of a heart is pierced. A distal anchoring member is engaged with a second wall of the heart chamber. A proximal anchoring member is engaged with the first wall of the heart chamber. A locking member affixed to a tether linking the proximal and distal anchors is pulled from an initial position between the two anchors to a locked position proximal the proximal anchor.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

The same reference numbers are used throughout the drawings to refer to the same parts.

DETAILED DESCRIPTION OF THE PRESENTLY PREFERRED EMBODIMENTS

Figure 1:
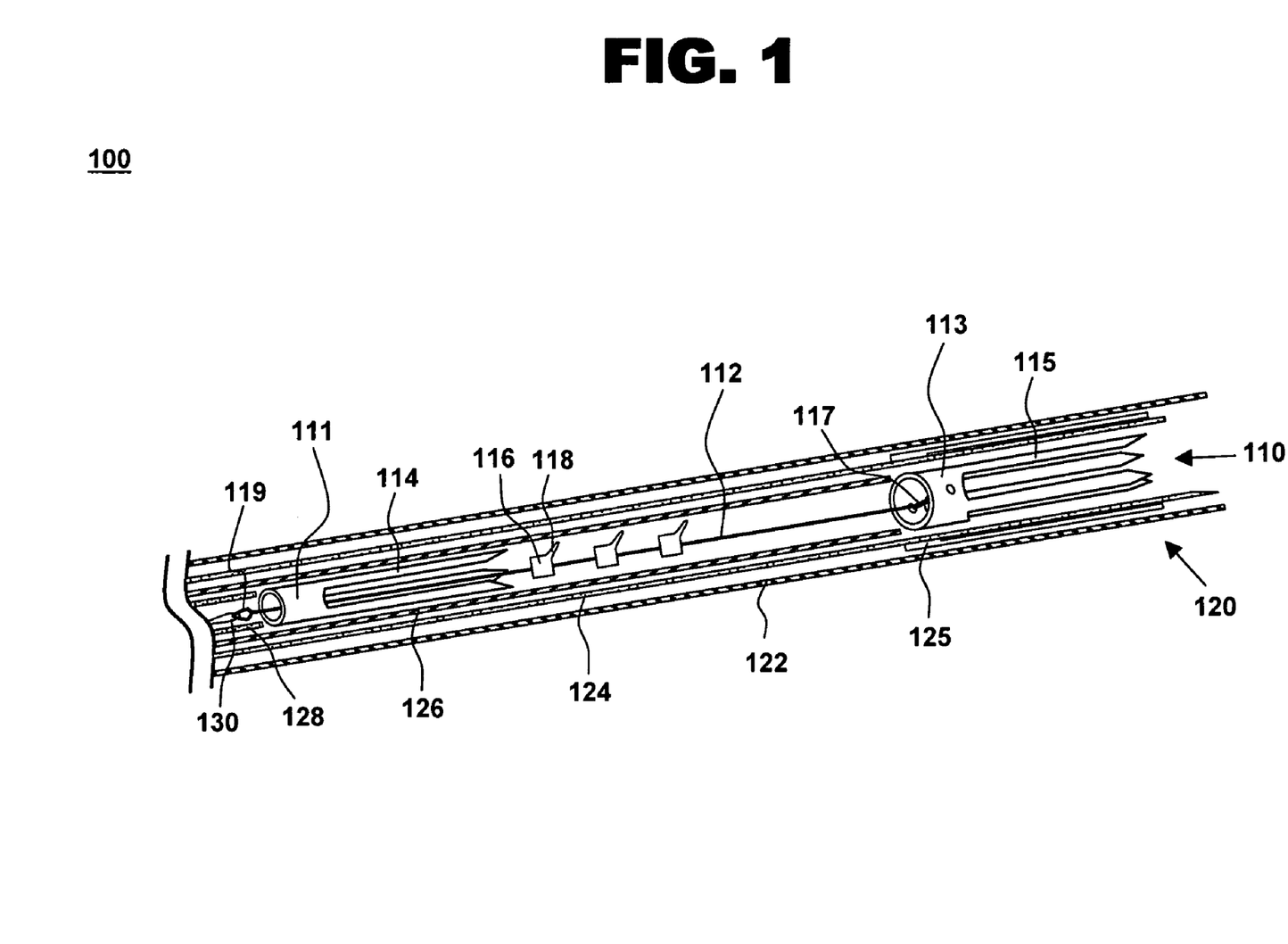
FIG. 1 is an isometric view of one embodiment of a tensioning device in accordance with the present invention, shown in the context of a system for treating mitral valve regurgitation in accordance with the present invention, the tensioning device being shown in toto, and a guiding catheter being shown in cross section.
Figure 2:
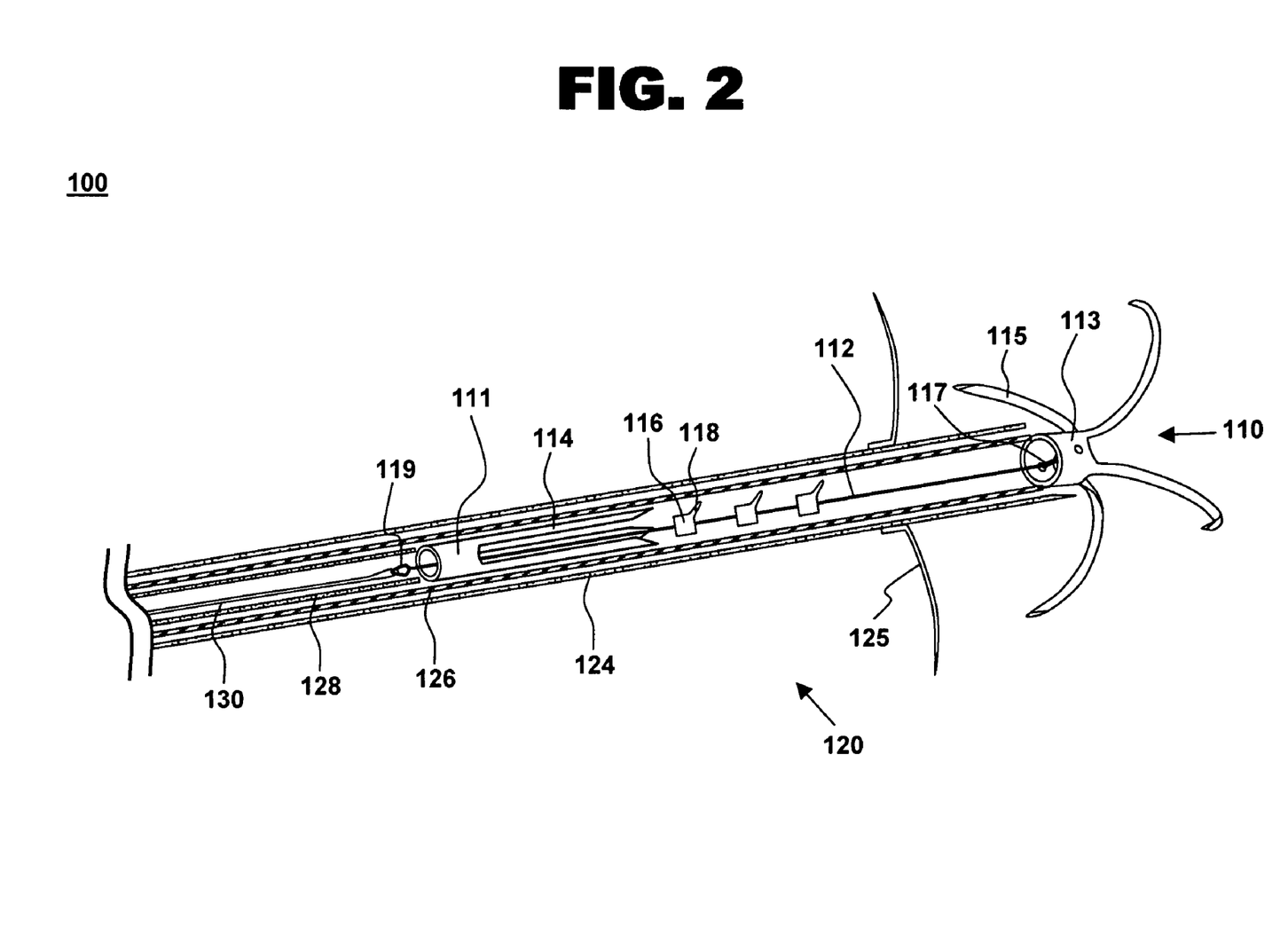
FIGS. 2 and 3 are isometric cutaway views of the device and system of FIG. 1 at two stages of deployment of the tensioning device.
Figure 3:
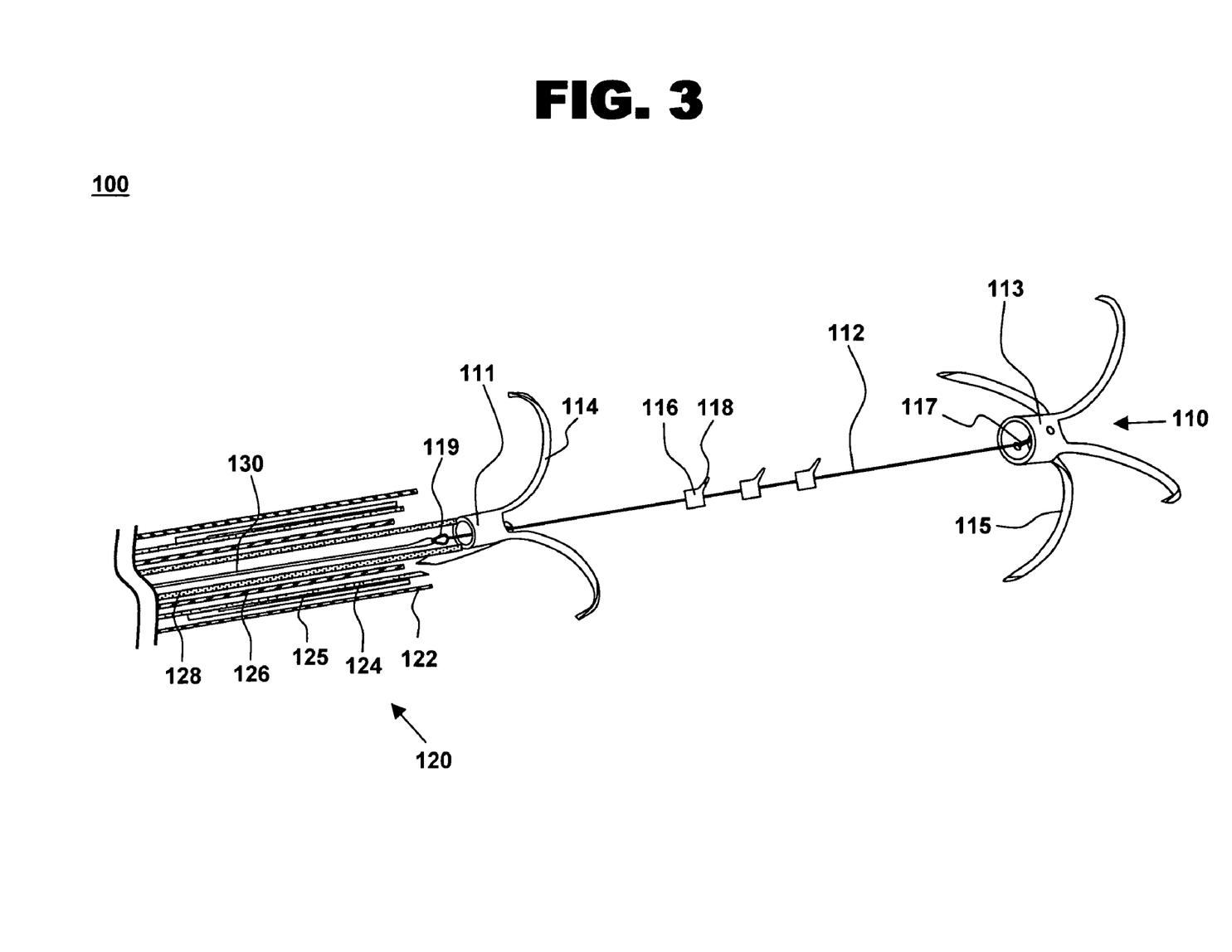

One aspect of the present invention is a tensioning device for treating mitral valve regurgitation. One embodiment of the device, in accordance with the present invention, is illustrated in FIGS. 1-3 at 110.

Tensioning device 110 is designed to be positioned across a chamber of a heart using minimally invasive catheterization techniques. Although described below in the context of treating mitral valve regurgitation by reducing or limiting lateral distension of the left ventricle as the heart beats, device 110 may be deployed at other locations in the heart and is readily adapted to a wide variety of uses, including treating ischemic or dilated cardiomyopathy.

Tensioning device 110 includes proximal anchoring member 111 positioned adjacent to the proximal end of tether 112, and distal anchoring member 113 positioned adjacent to the distal end of tether 112. As used herein, the terms "distal" and "proximal" are with reference to the treating clinician during deployment of the device.

At least one of the anchoring members includes an elastic portion that flexes in response to a heart beat when tensioning device 110 is positioned across the heart chamber. In the present embodiment, the elastic portion comprises a plurality of flexible arm segments. As tension is exerted on the device due to the motion of the beating heart, the arms flex, thereby providing a shock absorbing effect. This effect not only reduces the risk of tensioning device 110 failing due to structural fatigue, but also reduces localized compressive pressure on tissue against which the flexing anchoring member rests.

In the present embodiment, each of proximal and distal anchoring members 111 and 113 comprises a section of nitinol tubing having evenly spaced longitudinal slots cut into a distal portion of the tubing to form flexible arm segments 114 and 115, respectively. The slots may be, for example, rectangular, u-shaped, v-shaped, or Ω-shaped (omega-shaped). In another embodiment, the arm segments may be formed separately from the body of the anchoring member and assembled to create an integral whole. In either embodiment, the arm segments of the anchoring members comprise a biocompatible material capable of being preset into an anchor shape. Such materials include, but are not limited to, a nickel-titanium alloy, a nickel-cobalt alloy, another cobalt alloy, a thermoset plastic, stainless steel, a suitable biocompatible shape-memory material, a suitable biocompatible superelastic material, combinations thereof, and the like.

During manufacture, the arm segments are bent outward and heat set or otherwise set such that each of the arm segments is self-deploying radially outward at an angle of between 40 and 90 degrees from the longitudinal axis of the anchoring member when the anchoring member is released from delivery catheter 120. FIG. 1 shows the flexible arm segments in a radially compressed, folded configuration while the anchoring members are within delivery catheter 120. FIGS. 2 and 3 show the anchoring members self-expanded after having been released from delivery catheter 120, which is described below. For better viewing of device 110, the walls of the heart chamber across which tensioning member 110 is to be positioned are not shown in FIGS. 1-3.

In the present embodiment, proximal anchoring member 111 is intended to be deployed such that it is positioned with arm segments 114 resting against the right ventricular surface of the septal wall. In an alternative embodiment, proximal anchoring member 111 may be deployed such that arm segments 114 are embedded within the septal wall. For this embodiment, the arm segments would be directed proximally when in a radially compressed, folded configuration, rather than distally as shown in FIG. 1.

Figure 4A:
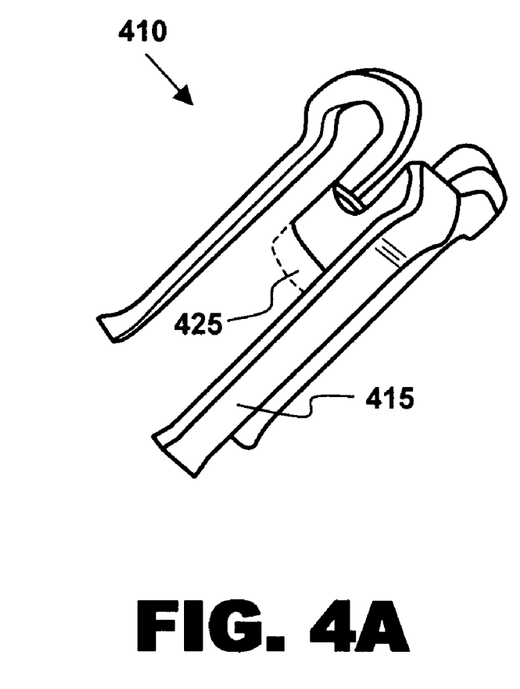
FIGS. 4A and 4B are isometric views of an alternative anchoring member in accordance with the present invention, showing the anchoring member in a compressed and an expanded configuration, respectively.
Figure 4B:
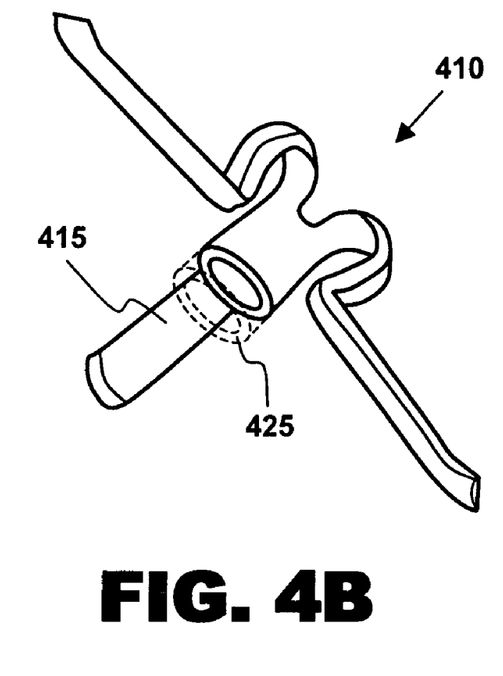

As illustrated in FIGS. 1-3, proximal anchoring member 111 includes three flexible arm segments 114 cut into a distal portion of the anchoring member. The number of arm segments may be varied, with the number, size, and shape of the arm segments selected to cover an area larger in diameter than the diameter of a hole that is pierced through the septal wall to deliver tether 112 and distal anchoring member 113 into the left ventricle. Proximal anchoring member 111 may also apply a contractive force around the hole, helping to prevent leakage of blood through the hole and eliminating the need for a sealing member. Tensioning device 110 may, however, include one or more sealing members adjacent to one or both of the anchoring members if desired. An example of a sealing member is shown in phantom at 425 in FIGS. 4A and 4B. Where an anchoring member is deployed within a wall, the anchoring member would not necessarily benefit from having a sealing member.

In the present embodiment, distal anchoring member 113 is intended to be released such that arm segments 115 expand radially within the tissue of (i.e., between the surfaces of) the outside or free wall of the left ventricle. Embedding the arm segments within the wall rather than positioning them against the outside surface of the wall reduces the risk of damage to structures beyond the wall such as the pericardial sac and the lungs. However, distal anchoring member 113 may be deployed outside the free wall if desired, with arm segments 115 resting against the outer surface of the wall. The arm segments would be directed proximally when in a radially compressed, folded configuration within the delivery catheter, rather than distally as shown in FIG. 1.

As illustrated in FIGS. 1-3, distal anchoring member 113 includes four flexible arm segments 115 cut into a distal portion of the anchoring member. The four-pronged shape of distal anchoring member 113 provides good retention within the free wall of the left ventricle; however, the number of arm segments may be varied.

In the present embodiment, only proximal anchoring member 111 flexes in response to a heart beat. Distal anchoring member 113 is not intended to flex within the tissue of the wall in which it is embedded. In another embodiment, in which distal anchoring member 113 is positioned outside the heart wall, both the proximal and distal anchoring members would flex in response to the motion of a beating heart.

One of ordinary skill in the art will recognize that the shapes of the anchoring members may be varied from those shown in FIGS. 1-3. For example, an alternative anchoring member 410 capable of flexing in response to a heart beat is shown in a radially compressed configuration in FIG. 4A and in a self-expanded configuration in FIG. 4B. In this design, the curve of each arm segment 415 is focused at the base of the segment, spreading the deflection load over roughly three-fourths of a circle.

When positioned across a heart chamber, the anchoring members and tether are under continuously varying tension due to the motion of the beating heart. To withstand this environment, tether 112 comprises a biocompatible metallic or polymeric material that combines flexibility, high strength, and high fatigue resistance. For example, tether 112 may be formed using materials such as stainless steel, titanium, a nickel-titanium alloy, a nickel-cobalt alloy, another cobalt alloy, tantalum, polypropylene, polyethylene, polyurethane, polytetrafluoroethylene (PTFE), polyester (Dacron®), nylon, combinations thereof, and the like. In one embodiment, tether 112 may comprise a polymeric filament having an elastic property that decreases linearly or in an abrupt step when a desired tether length is reached. Tether 112 may also comprise a pseudo-elastic nickel-titanium wire that has a helical shape (such as is seen in a portion of tether 512 of FIGS. 5A and 5B) and permits changes in length in response to varying tension loads. When the helix is straightened, the elastic property of the tether decreases, preventing lateral distension of the heart chamber beyond a set limit.

An antithrombotic component may be included in the chemical composition of a polymeric filament. Alternatively, a polymeric or metallic tether may be coated with a polymer that releases an anticoagulant and thereby reduces the risk of thrombus formation. If desired, additional therapeutic agents or combinations of agents may be used, including antibiotics and anti-inflammatories.

Distal anchoring member 113 is fixedly attached to tether 112 using a pin 117 that extends through the anchoring member and to which the tether is attached. Other methods of attaching distal anchoring member 113 to tether 112 include having an enlarged distal portion of tether 112 positioned distal to the distal anchoring member. Thus, tether 112 passes through a central lumen of distal anchoring member 113, and the enlarged distal portion of tether 112 prevents the tether from separating from the distal anchoring member. The distal enlargement may be a knot, a bead, or an enlargement mounted onto or formed into the tether.

Proximal anchoring member 111 is variably attached to tether 112 by a locking member affixed to tether 112. At least one locking member is drawn from an initial position between the two anchoring members to a position proximal the proximal anchoring member. This not only locks the proximal anchoring member onto the tether, but also adjusts the length of the tether to change the proximity of the anchoring members one to the other.

In the present embodiment, multiple locking members 116 are spaced apart on tether 112 between proximal anchoring member 111 and distal anchoring member 113, affixed by, for example, crimping or swaging the locking members onto the tether, confining each locking member with a knot or other enlargement on either side of the locking member, or using an adhesive. The length of the tether between the two anchoring members is adjusted and maintained at the chosen length by drawing an appropriate number of locking members through a central lumen of proximal anchoring member 111.

As shown in FIGS. 1-3, the locking members are formed of short sections of tubing having an outer diameter selected to provide a close sliding fit with the inner diameter of proximal anchoring member 111. Each locking member includes a flexible tab 118 flaring out at an angle from the longitudinal axis of the locking member. The tab extends from the distal end of the locking member and flares out at approximately a 45-degree angle. The locking member comprises a shape-memory material, and the tab is heat set or otherwise set into its flared position.

As a locking member is drawn through the lumen of proximal anchoring member 116, its tab is bent back into alignment with the body of the locking member in order to fit through the lumen. Once proximal to the anchoring member and no longer constrained by the lumen of proximal anchoring member 116, the tab resumes its preset shape. The flaring tab prevents the locking member from passing back through the proximal anchoring member, thereby locking proximal anchoring member 116 onto tether 112.

Figure 5A:
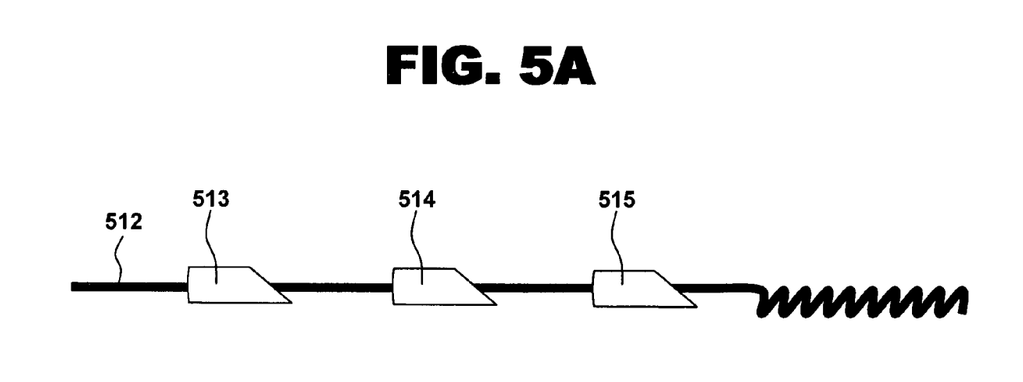
FIGS. 5A and 5B are side views of a tether portion and alternative locking members in accordance with the present invention, showing the locking members in unlocked and locked configurations, respectively.
Figure 5B:
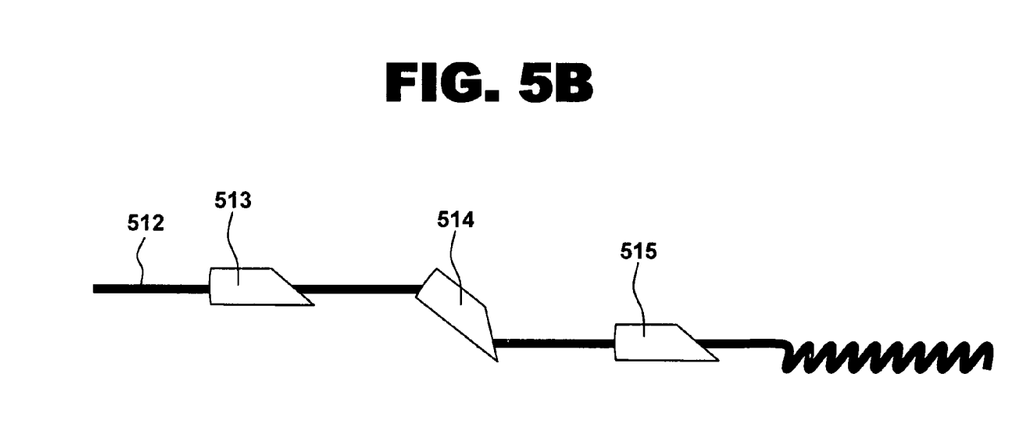

Any mechanism allowing tether motion in a proximal direction and preventing tether motion in a distal direction is suitable for the locking member. For example, locking members may be as shown in FIGS. 5A and 5B at 513, 514, and 515. Each locking member is formed of a short section of tubing that is cut at a 90-degree angle at the proximal end and at an angle of approximately 45 degrees at the distal end. The outer diameter of the locking member is selected to fit slidingly through the lumen of the proximal anchoring member. In order to set the tether length, the tether and at least one locking member are drawn proximally through the lumen of the proximal anchoring member. When the desired length of tether remains between the proximal and distal anchoring members, tether 512 is allowed to move in a distal direction until the locking member proximally adjacent to the proximal anchoring member engages the anchoring member, causing the locking member to cock at an angle, as shown by locking member 514 in FIG. 4B. At this angle, the elliptical distal face of locking member 514 abuts the proximal end of the proximal anchoring member, and the major axis of the locking member elliptical distal end is greater than the inside diameter of the proximal anchoring member. Consequently, the locking member cannot be drawn distally through the anchoring member at the angle shown in FIG. 5B. However, if the treating clinician wishes to readjust the locked tensioning device to increase the length of the tether between the proximal and distal anchoring members, tether 512 can be again pulled in a proximal direction, thereby straightening locking member 514 to the configuration shown in FIG. 5A and freeing it from engagement with the proximal anchoring member. Locking member 514 can then pass distally back through the proximal anchoring member. Thus, the length of the tether may be readjusted and relocked.

Tether 112 includes a loop 119 on the proximal end of the tether. A length of suture material or another strong, thin, filament 130 passes through loop 119. The filament is roughly doubled over onto itself with the ends of the filament adjacent to each other and two portions of the filament extending away from loop 119. The filament is sized such that the ends of the filament extend outside the patient when tensioning device 110 is positioned at the treatment site. A treating clinician pulls both ends of the filament simultaneously to draw the appropriate number of locking members through proximal anchoring member 111. Once the length of the tether has been adjusted and proximal anchoring member 111 has been locked onto tether 112, filament 130 is removed by releasing one end of the filament and pulling on the other end until the filament is withdrawn from the patient. This design eliminates the need to thermally cut or otherwise sever tether 112 after tensioning device 110 has been deployed at the treatment site.

Other arrangements may be used to releasably engage a draw filament with the tether of a tensioning device such as is described herein. Examples include a ball and a socket, a hook and a ring, and a collet and a pin.

To ensure proper positioning, it is desirable that tensioning device 110 be visible using fluoroscopy, echocardiography, intravascular ultrasound, angioscopy, or another means of visualization. Where fluoroscopy is utilized, any or all of tensioning device 110 may be coated with a radiopaque material, or a radiopaque marker may be included on any portion of the device that would be useful to visualize.

Another aspect of the present invention is a system for treating mitral valve regurgitation that includes tensioning device 110 described above. The system, shown generally by numeral 100 in FIGS. 1-3, further includes delivery catheter 120.

Tensioning device 110 is slidably received within a lumen of delivery catheter 120 for delivery to and deployment at the treatment area. As best seen in FIG. 1, delivery catheter 120 comprises guiding sheath 122, piercing tube 124, holding tube 126, and push cylinder 128. Piercing tube 124 is slidable within a lumen of guiding sheath 122, holding tube 126 is slidable within a lumen of piercing tube 124, and push cylinder 128 is slidable within a lumen of holding tube 126. Thus, delivery catheter 120 comprises four separate, concentric members, each slidable to be individually extended or retracted as needed to deliver tensioning device 110.

Guiding sheath 122 comprises a flexible, biocompatible material such as polyurethane, polyethylene, nylon, or polytetrafluoroethylene (PTFE). Guiding sheath 122 has a preformed or steerable distal tip that is capable of assuming a desired bend with respect to the longitudinal axis of the sheath, for example, a ninety-degree bend.

Piercing tube 124 comprises the same or a different biocompatible material from that used to form guiding sheath 122. In the present embodiment, the distal end of piercing tube 124 is angle-cut to form a sharp edge able to pierce into or through myocardial tissue. Thus, where tensioning member 110 is to be delivered transluminally, piercing tube 124 must be flexible enough to be delivered through vasculature to the treatment area while still rigid enough to pierce myocardial tissue.

Piercing tube 124 may include a stop collar 125 to aid in positioning distal anchoring member 113 by controlling the depth of penetration of piercing tube 124 into the wall. A proximal portion of stop collar 125 is attached to the outside surface of a distal portion of piercing tube 124. Stop collar 125 is cylindrical and has longitudinal slots spaced around a distal portion of the cylinder to form segments that are heat set or otherwise set such that they flare out away from the longitudinal axis of the cylinder when stop collar 125 is released from guiding sheath 122. Stop collar 125 is seen contained within the lumen of guiding sheath 122 in FIG. 1 and self-expanded into its preset flared configuration in FIG. 2. In FIG. 3, stop collar 125 has been retracted back within guiding sheath 122 and is again radially compressed within the lumen of guiding sheath 122.

Holding tube 126 and push cylinder 128 also comprise one or more biocompatible materials. Push cylinder 128 may be either a hollow or a solid elongated cylinder. Both holding tube 126 and push cylinder 128 must be flexible while still having sufficient rigidity to exert force on a heart chamber wall or an anchoring member, as described below.

An alternative embodiment of the system (not shown) resembles the embodiment described above, except that the tensioning device does not include locking members initially positioned between the proximal and distal anchoring members. In this embodiment, a locking member may be positioned proximal to the proximal anchoring member and be locked onto one or both of the tether and the proximal anchoring member to hold the tensioning device at a desired length. Alternatively, the tensioning device may be a preset length having a tether that is not adjustable.

Figure 6:
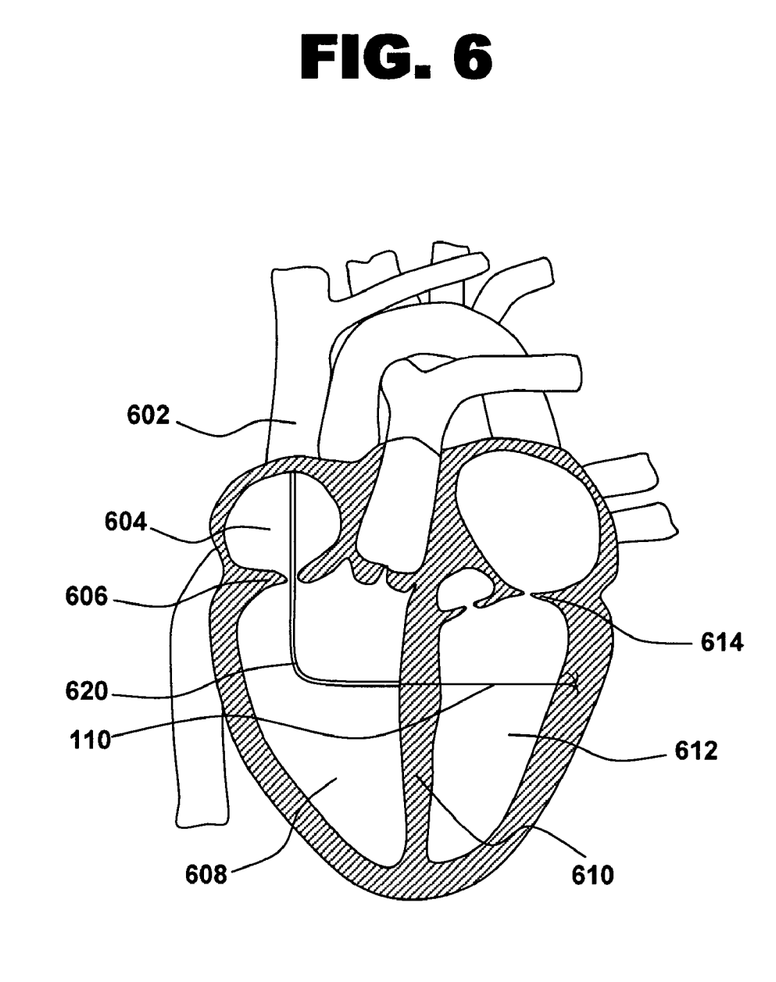
FIG. 6 is a schematic view illustrating the placement of the tensioning device across a left ventricle, in accordance with the present invention.
Figure 7:
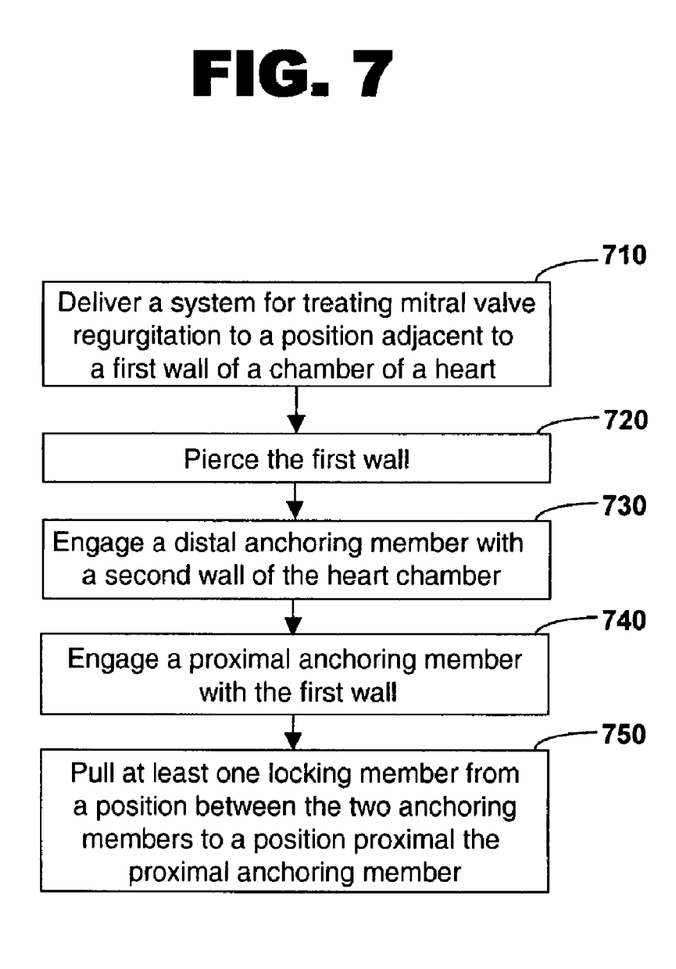
FIG. 7 is a flow diagram of one embodiment of a method for treating mitral valve regurgitation by affecting a mitral valve annulus, in accordance with the present invention.

Another aspect of the present invention is a method for treating mitral valve regurgitation by affecting a mitral valve annulus. FIG. 6, which shows a system for treating mitral valve regurgitation at an intermediate step of the method, is used throughout the following discussion as a reference for the structures of the heart. FIG. 7 shows a flow diagram of one embodiment of the method in accordance with the present invention.

A system for treating mitral valve regurgitation is delivered to a position adjacent to a first wall of a chamber of a heart (Block 710). In the present embodiment, the system is system 100, as described above, and the first wall is the septal wall between the right and left ventricles of the heart.

For delivery, system 100 is in the configuration shown in FIG. 1. Tensioning device 110 is slidably received within delivery catheter 120. Arm segments 114 and 115 of proximal anchoring member 111 and distal anchoring member 113, respectively, are in a folded, radially compressed configuration. Proximal anchoring member 111 is positioned within the lumen of holding tube 126, while distal anchoring member 113 is positioned within the lumen of piercing tube 124. Push cylinder 128 abuts the proximal end of proximal anchoring member 111. Holding tube 126 abuts the proximal end of distal anchoring member 113.

Delivery catheter 120 carrying tensioning device 110 is passed through the venous system and into a patient's right ventricle. This may be accomplished as shown in FIG. 6, in which delivery catheter 120 has been inserted into either the jugular vein or the subclavian vein and passed through superior vena cava 602 into right atrium 604, and then passed through tricuspid valve 606 into right ventricle 608. Alternatively, the catheter may be inserted into the femoral vein and passed through the common iliac vein and the inferior vena cava into the right atrium, then through the tricuspid valve into the right ventricle. The procedure may be visualized using fluoroscopy, echocardiography, intravascular ultrasound, angioscopy, or other means of visualization.

The distal tip of delivery catheter 120 is positioned against the right ventricular surface of the septal wall. As described above, guiding sheath 122 of delivery catheter 120 includes a preformed or steerable distal tip that allows the delivery catheter to approach septal wall 610 in a desired orientation, for example at a 90-degree bend as shown in FIG. 6.

Delivery catheter 120 pierces the septal wall (Block 720). This is accomplished by extending piercing tube 124 beyond the distal end of guiding sheath 122 until the tube pierces through the septal wall.

A distal anchoring member is then engaged with a second wall of the heart chamber (Block 730). In the present embodiment, distal anchoring member 113 is engaged with the free wall of left ventricle 612 by being embedded within (i.e., between the surfaces of) the wall. To accomplish this, piercing tube 124 is advanced across the left ventricle and allowed to pierce into the free wall of left ventricle 612. Stop collar 125, which is attached to the outside surface of a distal portion of piercing tube 124, remains constrained as seen in FIG. 1 until it exits the septal wall, at which time it is free to self-expand into its preset configuration, as seen in FIG. 2. The expanded stop collar rests against the inside surface of the free wall of the left ventricle, controlling the depth of penetration of piercing tube 124 into the wall and ensuring arm segments 115 are embedded between the two surfaces of the wall rather than extending through the wall. Guiding sheath 122 is not seen in FIG. 2 as it remains in right ventricle 608, supporting the delivery system while piercing tube 124 and its contents are advanced through the septal wall and across the left ventricle.

Distal anchoring member 113 is then pushed out of piercing tube 124 using holding tube 126, at which time arm segments 115 are permitted to expand away from the body of distal anchoring member 113 and fix the distal anchoring member firmly within the wall. FIG. 2 shows distal anchoring member 113 in its self-expanded configuration, having been released from delivery catheter 120. Holding tube 126 is seen extended and resting against the proximal end of distal anchoring member 113. FIG. 6 also shows system 100 at this stage of deployment of tensioning member 110.

Alternatively, distal anchoring member 113 may be delivered by extending piercing tube 124 to penetrate into or through the free wall of the left ventricle, and then retracting piercing tube 124 while holding distal anchoring member 113 stationary with holding tube 126. Distal anchoring member 113 is thus released from the distal end of piercing tube 124 and permitted to self-expand within or beyond the wall. This alternative should be used where distal anchoring member 113 is to be positioned resting against the outside surface of the free wall.

Following deployment of the distal anchoring member, piercing tube 124 is withdrawn across the left ventricle, through the septal wall, and into guiding sheath 122. Tether 112, which links distal anchoring member 113 with proximal anchoring member 111, is allowed to play out transverse the left ventricle as piercing tube 124 is withdrawn. Stop collar 125 returns to a radially compressed configuration as it passes through the septal wall and reenters the lumen of guiding sheath 122.

Proximal anchoring member 111 is then deployed such that it engages with the septal wall (Block 740). To accomplish this, proximal anchoring member 111 is pushed out of holding tube 126 using push cylinder 128, or holding tube 126 is withdrawn while proximal anchoring member 111 is maintained stationary with push cylinder 128. Proximal anchoring member 111 is thus released from the distal end of piercing tube 124 and permitted to self-expand as seen in FIG. 3, either within or adjacent to septal wall 610.

After proximal anchoring member 111 has been deployed, a locking member affixed to a tether linking the distal and proximal anchoring members is pulled from an initial position between the two anchoring members to a locked position proximal the proximal anchoring member (Block 750). In the present embodiment, holding tube 126 is extended to rest against the expanded proximal anchoring member and act as a brace while tether 112 is being pulled in a proximal direction to adjust the tether to the desired length.

Shortening the length of the tether between the two anchoring members draws the walls of the left ventricle together and reduces both the radial tension on and the radial dimension of the mitral valve (seen in FIG. 6 at 614), thus improving coaptation of the valve leaflets and reducing regurgitation. At least one of the anchoring members, in the present embodiment the proximal anchoring member, flexes in response to a heart beat when the anchoring members and tether are positioned across the heart chamber. This provides a shock absorbing effect that helps to protect the tensioning device from fatigue and reduces localized compressive pressure on tissue against which the flexing anchoring member rests.

The tensioning device may be placed in close proximity to the mitral valve, so that when the length of the tether between the proximal and distal anchoring members is adjusted, the outer cardiac wall is drawn toward the septal wall such that the anterior and posterior leaflets of the mitral valve are drawn together, thus reducing regurgitation. Alternatively, the tensioning device may be positioned across the left ventricle at an angle such that, for example, only one end of the device is anchored as close to the mitral valve annulus as possible. Two or more tensioning devices may also be placed across the left ventricle in parallel, crisscrossing, or in other patterns as believed by the treating clinician to best achieve the desired result of radially compressing or relieving tension from the mitral valve. Alternatively, or in addition to ventricular placement, a tensioning device of the invention may be deployed across the left atrium, as approached from the right atrium, to radially compress or relieve tension from the mitral valve.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for treating mitral valve regurgitation comprising:
    a tensioning device comprising a tether, a distal anchoring member positioned adjacent to a distal end of the tether and a proximal anchoring member positioned adjacent to a proximal end of the tether, wherein at least one of the anchoring members includes an elastic portion that flexes in response to a heart beat when the tensioning device is positioned across a chamber of a heat; and
    a delivery catheter, wherein the tensioning device is slidably received within a lumen of the delivery catheter, wherein the delivery catheter comprises a guiding sheath, a piercing tube slidably received within a lumen of the guiding sheath, a holding tube slidably received within a lumen of the piercing tube, a push cylinder slidably received within a lumen of the holding tube and a stop collar attached to an outside surface of a distal portion of the piercing tube, and wherein a portion of the stop collar is self-expanding when the stop collar is positioned outside the lumen of the guiding sheath.

2. A system for treating mitral valve regurgitation, comprising:
    a delivery catheter; and
    a tensioning device received in the delivery catheter, the tensioning device including a tether, a distal anchoring member positioned adjacent to a distal end of the tether, a proximal anchoring member positioned adjacent to a proximal end of the tether, and at least one locking member affixed to the tether; wherein when the locking member is pulled from an initial position between the anchors to a locked position proximal the proximal anchoring member, the length of the tether is adjusted to change the proximity of the anchoring members one to the other,
    wherein the delivery catheter comprises a guiding sheath, a piercing tube slidably received within a lumen of the guiding sheath, a holding tube slidably received within a lumen of the piercing tube, a push cylinder slidably received within a lumen of the holding tube and a stop collar attached to an outside surface of a distal portion of the piercing tube, and wherein a portion of the stop collar is self-expanding when the stop collar is positioned outside the lumen of the guiding sheath.

3. The system of claim 2 wherein the tether includes a release loop adjacent to a proximal end of the tether.

4. The system of claim 2 wherein the locking member comprises a generally cylindrical member having a flexible tab flaring out from the cylindrical member.

5. The system of claim 2 wherein the locking member comprises a generally cylindrical member having an end shaped to form an angle with the longitudinal axis of the cylindrical member that is less than 90 degrees.

6. The system of claim 2 wherein at least one of the anchoring members includes an elastic portion that flexes in response to a heart beat when the tensioning device is positioned across a chamber of a heart.

7. The system of claim 6 wherein the elastic portion of the at least one anchoring member comprises a material selected from a group consisting of a nickel-titanium alloy, a nickel-cobalt alloy, a cobalt alloy, a thermoset plastic, stainless steel, a biocompatible shape-memory material, a biocompatible superelastic material, and a combination thereof.

8. The system of claim 6 wherein the elastic portion comprises a plurality of flexible arm segments.

9. The system of claim 8 wherein the flexible arm segments are in a radially compressed, folded configuration while the anchoring member is within a lumen of the delivery catheter and wherein the flexible arm segments self-expand when the anchoring member is released from the delivery catheter.

10. The system of claim 8 wherein the flexible arm segments of at least one of the anchoring members self-expand.

11. The system of claim 2 wherein the tether comprises a material selected from a group consisting of stainless steel, titanium, a nickel-titanium alloy, a nickel-cobalt alloy, a cobalt alloy, tantalum, polypropylene, polyethylene, polyurethane, polytetrafluoroethylene (PTFE), polyester (Dacron®), nylon, a flexible and strong biocompatible material, and a combination thereof.

12. The system of claim 2 wherein at least a portion of the tensioning device includes a therapeutic agent selected from a group consisting of an antithrombotic, an anticoagulant, and a combination thereof.

13. The system of claim 2 wherein the tensioning device includes at least one sealing member.

* * * * *